United States Patent [19]

Caveney et al.

[11] Patent Number: 4,633,413

[45] Date of Patent: Dec. 30, 1986

[54] DIGITAL DILUTION APPARATUS AND METHOD

[75] Inventors: Robert Caveney, San Jose; Dana Gilliam, Sunnyvale; Melvin Chan, Daly City; Michael Bailey, Santa Cruz, all of Calif.

[73] Assignee: Cavro Scientific Instruments, Sunnyvale, Calif.

[21] Appl. No.: 518,217

[22] Filed: Jul. 28, 1983

[51] Int. Cl.[4] .......................... G06F 15/42; B67D 5/30
[52] U.S. Cl. ................................ 364/500; 73/864.16; 73/863.01; 73/864.12
[58] Field of Search ............... 364/500, 501, 496, 497; 422/81, 68, 69, 72; 73/864.12, 864.11, 864.21, 863.01, 864.16

[56] References Cited

U.S. PATENT DOCUMENTS

| | | | |
|---|---|---|---|
| 3,842,679 | 10/1974 | Iwao et al. | 73/864.21 |
| 4,026,665 | 5/1977 | Mansfield et al. | 364/499 X |
| 4,252,769 | 2/1981 | Hood et al. | 422/68 X |
| 4,254,460 | 3/1981 | Achter et al. | 364/500 X |
| 4,281,387 | 7/1981 | Kraft et al. | 364/497 |
| 4,346,742 | 8/1982 | Chase et al. | 73/864.12 X |
| 4,441,374 | 4/1984 | Suzuki | 422/81 |
| 4,475,666 | 10/1984 | Bilbrey et al. | 73/864.16 X |

OTHER PUBLICATIONS

New Instrumentation Preview, Flexigem; Paul Philip Sher, MD, The Journal of Clinical Laboratory Automation, vol. 2, No. 3; 169-173, (1982 May/Jun.).

Primary Examiner—Edward J. Wise
Attorney, Agent, or Firm—Flehr, Hohbach, Test, Albritton & Herbert

[57] ABSTRACT

Digital dilution apparatus is disclosed which performs multiple processing functions such as pipetting, diluting, titrations and the like under microprocessor control. The apparatus is responsive to operator-entered processing requests and performs complex and accurate processing functions. The disclosed apparatus is quite simple and easy to operate and does not require a highly skilled operator.

25 Claims, 11 Drawing Figures

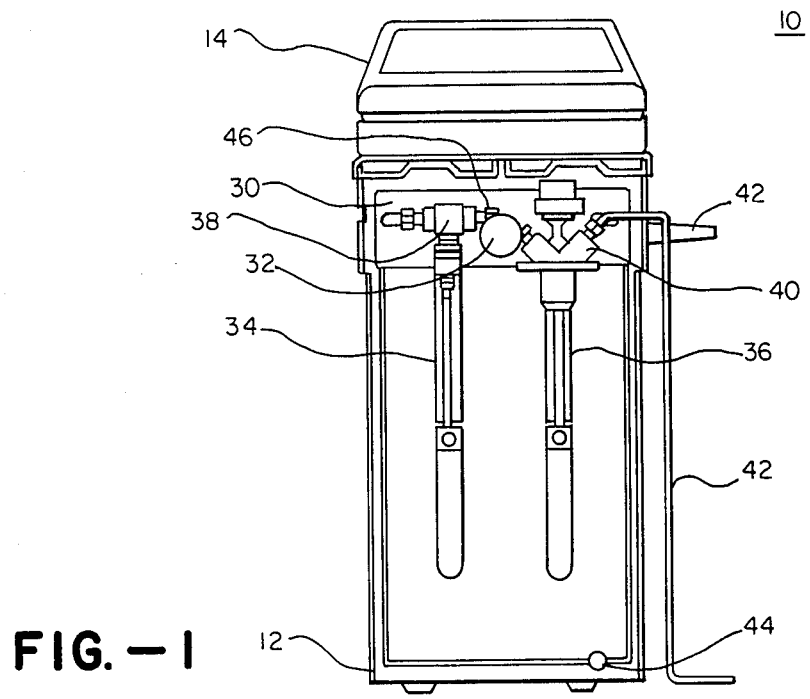
FIG.—1
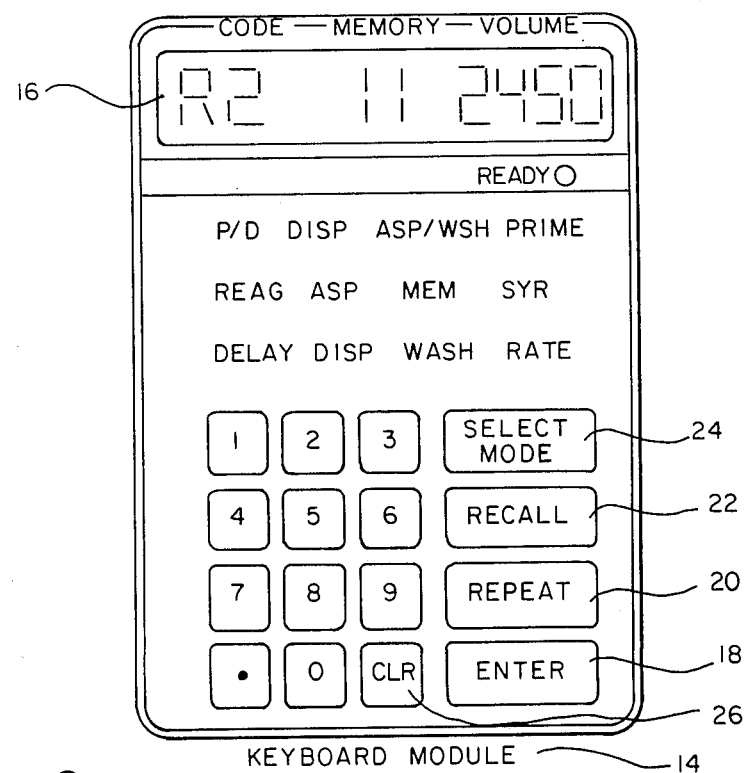
FIG.—2

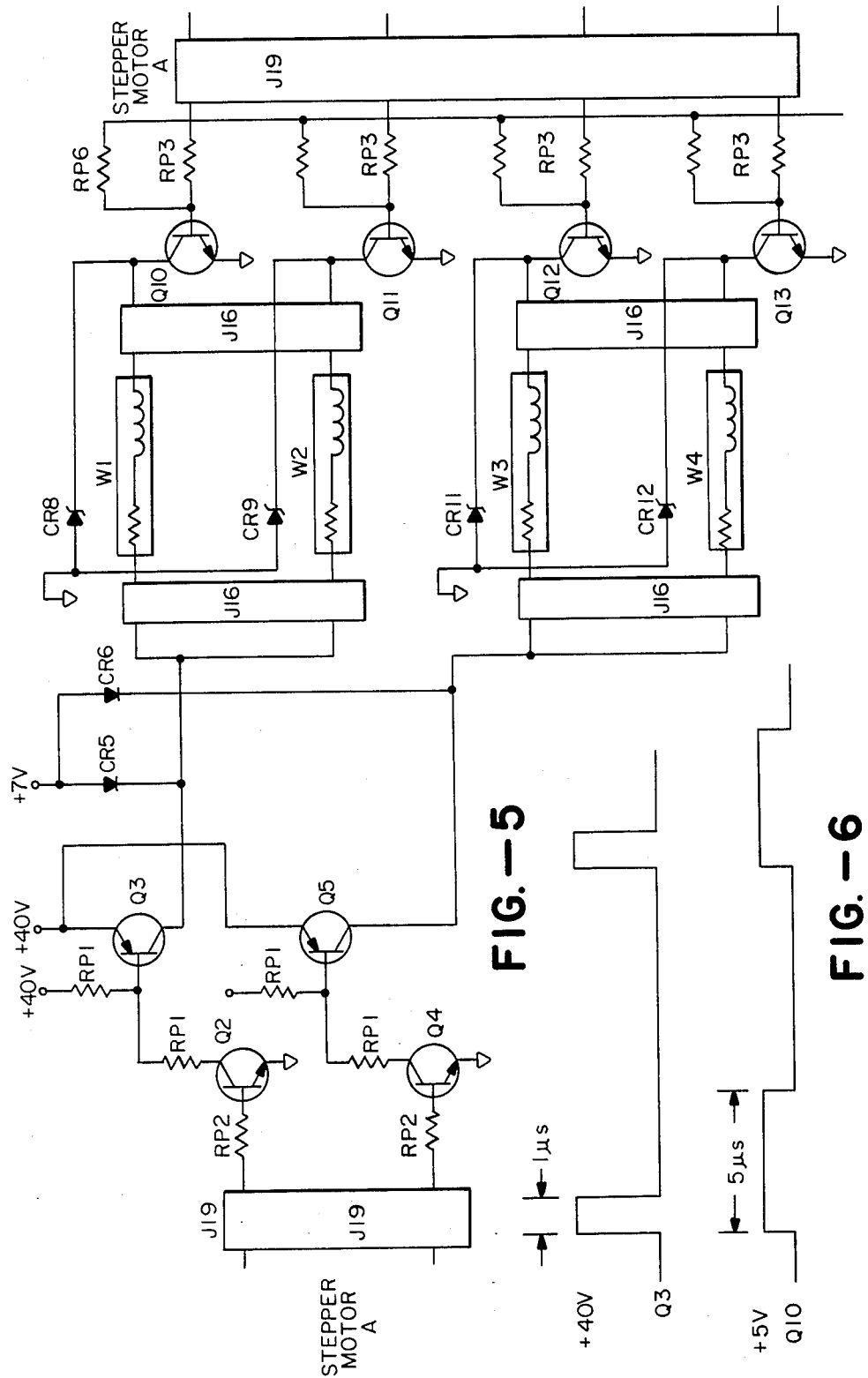
FIG.—5
FIG.—6

DIGITAL DILUTION APPARATUS AND METHOD

BACKGROUND OF THE INVENTION

The present invention relates to digital dilution apparatus and method therefor.

In the prior art, digital dilution equipment is known which processes important liquid sample processing functions such as pipetting, diluting, dispensing, titrating and sample only transferring. The dilution apparatus must be able to process these functions accurately and precisely yet while operating with extremely small volumetric ranges (e.g., microliters to milliliters).

A problem with such dilution equipment is the difficulty of providing suitable "interfacing" between an operator and the particular liquid sample to be processed. Some prior art devices are quite complex, requiring many steps of operation from a user or operator in order to perform the desired function or functions (i.e., the operator must know each sequence of steps in the overall operation and be able to input these steps into the system, which requires a detailed knowledge and capability of working with the system). While prior art devices are known which provide fewer processing functions, such devices are inherently limited in their overall capability.

In effect, the prior art does not, in general, have the capability of communicating, on an intelligent level, with an operator who may not possess the necessary expertise described above to effect the desired processing functions. For instance, if an operator desires to have a processing function performed, such as pipette and/or dilute, the prior art equipment typically requires that the operator have considerable background expertise in order to achieve the desired pipette/dilute function. The prior art equipment cannot communicate on an intelligent level with an operator not having the necessary expertise in order to complete the desired processing functions. Consequently, some dilution processing functions may not be possible with such prior art equipment, if a highly skilled operator is unavailable.

As indicated above, it is most important that the desired processing functions be performed accurately and, of course, precisely. One very apparent difficulty is the very small volumetric ranges with which an operator must work when performing one or more of the desired processing functions indicated above. Prior art equipment has not in general been able to provide such an accurate and precise processing capability with very small volumes while at the same time providing apparatus which is in general quite simple and easy to operate.

It would be highly desirable to provide improved digital dilution equipment which can communicate with an operator to effect, in a straightforward, precise and accurate fashion, the processing of any number of a plurality of liquid sample processing functions such as described above. More particularly, it would be desirable to provide improved dilution equipment which can effectively "lead" an operator through the necessary steps in order to achieve the specific processing functions.

In view of the foregoing background, it is an objective of the present invention to provide improved digital dilution apparatus and method therefor.

SUMMARY OF THE INVENTION

The improved digital dilution apparatus according to the present invention includes memory means for storing a series of programmed instructions and input means for communicating operator-controlled general dilution processing requests to the memory means.

The apparatus also includes output means and means responsive to the dilution processing requests for generating a series of communications to the output means inquiring of the specific nature of the processing request. The output means typically could be a display panel for displaying the communication inquiries to an operator.

The displayed communications in effect "lead" the operator through a series of simple and logical processing requests in order to initiate the desired function, such as dispensing or titrating. Hence, the apparatus also includes means for entering operator controlled specified processing requests to the memory means which is responsive to the entered requests for processing the specified dilution processing requests.

In accordance with the foregoing summary, the present invention achieves the objective of providing an improved digital dilution apparatus.

Other objects and features of the present invention will become apparent from the following detailed description of preferred embodiments when taken in conjunction with the accompanying drawings.

BRIEF DESCRIPTION OF THE DRAWINGS

FIG. 1 depicts a front view of a digital pipetter/dilutor according to the present invention.

FIG. 2 depicts a front panel display of the control module of FIG. 1.

FIG. 5 depicts a schematic diagram for a stepper motor drive circuit.

FIG. 6 depicts the timing diagram for the stepper motor operation of FIG. 5.

DESCRIPTION OF THE DRAWINGS

Figure 3:
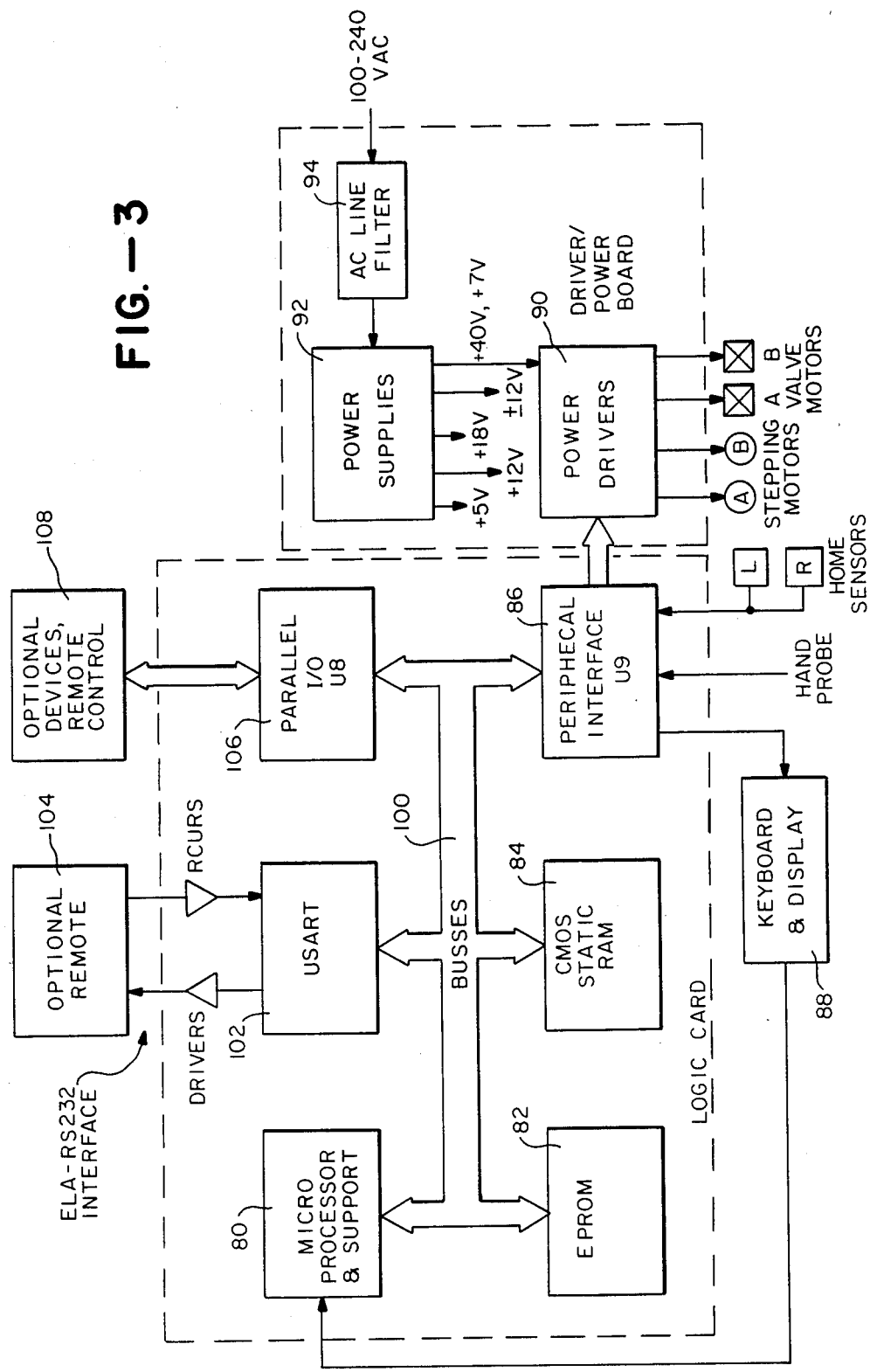
FIG. 3 depicts a block diagram of a control system to control the overall operation of the apparatus depicted in FIG. 1.

Referring now to FIG. 1, a front view of a digital pipetter/dilutor 10 according to the present invention is depicted.

In FIG. 1, the pipetter/dilutor system 10 includes the keyboard control module 14 affixed to a main assembly 12, typically with magnets. Control module 14 can be easily moved to any convenient location with a flexible telephone-like cord (not shown).

FIG. 1, the main assembly 12, includes an interchangeable fluid cassette 30 which is held in place to main assembly 12 by means of a cassette thumbscrew 32.

Mounted on each fluid cassette 30 is a reagent syringe 34 and a sample syringe 36.

Reagent syringe 34 includes a valve 38 which, as will be described, allows dispensing of reagent solutions under microprocessor control. An interconnect 46 provides the proper connections for valve 38.

Sample syringe 30 is connected to a cross flow manifold and syringe housing 40 which also, as will be described, provides for dispensing and pipetting of sample solutions under microprocessor control.

Sample syringe 36 can be connected to a dispense/sample tube 42 for connection to a hand probe (not shown) which provides for easy manual use by an operator. The hand probe can be placed in hand probe holder 42 when not in use.

The main assembly 12 also includes a power light 44 for visually indicating that power is on to an operator.

The pipetter/dilutor system depicted in FIG. 1 is an accurate, microprocessor-based dilutor, with motor driven valves and syringes. As will be described, in one preferred embodiment, up to 15 different programs or sequences can be entered by means of a keyboard entry in control panel 14, and stored indefinitely. Single operations can be entered and perform more accurately and more quickly than with manual prior art methods.

Referring now to FIG. 2, the front panel display of the control module 14 of FIG. 1 is depicted. The display panel depicted in FIG. 2 will provide the following operational modes:
1. PRIME: This mode flushes all tubing and syringes with reagent, and insures that all air and impurities are expelled.
2. P/D (Pipette/Dilute): This mode draws in a selected size sample from a hand probe and then draws in a selected amount of reagent and dispenses both through the hand probe.
3. DISP (Dispense): This mode draws in a selected amount of reagent, then dispenses that reagent through the hand probe.
4. ASP/WSH (Aspirate/Wash): This mode draws in a sample from a hand probe, dispenses that sample and then dispenses reagent to clean the system.

As will be discussed in more detail herein, there are complicated sequences of operation which can be easily programmed by an operator according to the present invention. Typical sequences are progressive size dispenses, progressive size samples, counted dispenses by specified number, additive dispenses (titrations), multiple sample aliquots, progressive size sample aliquots (serial dilutions), single sample transfer and wash, variable volume sample aliquot transfers, and infinite multiple aliquots of equal size.

The invention as depicted in FIG. 1 can be configured with a single syringe with or without the keyboard display depicted in FIG. 2, with a dual syringe with or without the keyboard, with master remote systems with up to five remotes or slaves from one keyboard, with custom systems with special programming, interfaced through an 8-bit parallel I/O port. Additional cassettes and syringes can be added to make quick changes in volumes aspirated and dispensed.

Typical syringe sizes which can be easily interchanged with the assembly 12 are as follows:

| Reagent Syringes | Sample Syringes |
| --- | --- |
| 10 milliliter | 1 milliliter |
| 5000 microliter | 500 microliter |
| 2500 microliter | 250 microliter |
| 1000 microliter | 100 microliter |
| 500 microliter | 50 microliter |
| 50 microliter | 10 microliter |

Referring again to FIG. 2, a front panel of control module 14 includes an 8-digit fluorescent panel 16 which displays digits as they are keyed so that they can be checked before they are entered into the system via the ENTER command key 18. Typical data that is entered into the system is aspiration rate, syringe sizes, sample and dispense volumes, number of repeats, and program number (memory number).

In FIG. 2, the display panel also includes command keys REPEAT 20, RECALL 22, and SELECT MODE 24, the functions of which will be described in more detail.

The display 14 also includes a standard 12-button key pad including numbers 0-9, a decimal point and a CLEAR key 26 for entering the necessary data into the system.

The four command keys, ENTER 18, REPEAT 20, RECALL 22, and SELECT MODE 24, have different functions, which are now described below:

The ENTER function is used after data has been keyed into the system. The ENTER function tells the system that the statement has been finished (such as the reagent rate to be dispensed) and the operator is ready to move on to another statement. The system will wait until the ENTER key 18 is touched, accept the volume indicated in display 16, at which time the system will continue to the next phase of the "program."

The ENTER key 18 is also used for an EDIT function and, in addition, for reviewing the content of the memory. By pressing the ENTER key 18, a program phase is lit and the display will show the volume, memory location and code for that particular phase.

Referring again to FIG. 2, the display portion 16 is divided into three sections, each of which provides information during all or various portions of a particular procedure. From left to right, the sections in FIG. 2 are CODE, MEMORY, and VOLUME. Each of these functions provide information to an operator as follows:

VOLUME: The volume function of the display is read in a preferred embodiment in microliters. There is provided in display 16 a total of five digits so that the maximum reading for one embodiment is 9,999 microliters. Portions of that code display change with each phase of a procedure which assists an operator in keeping track of what phase he is working with, in case of interruption.

MEMORY: The memory function of display 16 shows a number which, in one embodiment, provides up to 15 specific programmed memory locations being utilized. When the system is programmed from a "fresh start," the system employs a scratch pad memory, which is known in the art. In such a case, the system is not working with a specific memory location, and the memory portion of the display 16 is blank. The scratch pad operation will be discussed below.

CODE: The code function is the location where the REPEAT or ERROR codes appear. When ERROR code is shown, the system is disabled until it is cleared and corrected. The REPEAT code will be discussed in more detail below.

Also depicted in FIG. 2 are eight function arrays, which are REAG, ASP, MEM, SYR, DELAY, DISP, WASH, and RATE.

In the REAG phase of a program, the instrument is displaying the amount of reagent (or buffer or diluent) to be used in a particular procedure.

In the REAG+SYR phase, the instrument displays the size of the reagent syringe.

In the ASP phase, the instrument shows the amount of liquid to be aspirated from a hand probe.

In the ASP SYR phase, the instrument displays the sample or aspiration syringe size.

In the DELAY phase, the instrument provides for a timed delay period before dispensing from the hand probe, which is particularly useful in kinetic reactions.

In the REAG Rate phase, the display 16 lights when the instrument is telling the rate or speed when the reagent is being drawn into a reagent syringe. It should be noted that that is not the dispense rate. The REAG RAte phase is useful when the rate of intake must be quick in order to vary overall procedure speed, but the dispense rate must be different for reasons of mixing receptacle size or shape. The ASP rate is the speed at which the sample syringe draws in a particular sample. It is also the speed employed to expel the sample.

The DISP RATE phase is the speed which is programmed to expel the reagent from the reagent syringe through a hand probe. It should be noted that all rates are expressed, in the present invention, in single digit numbers 0 through 9. The operator should think of these numbers as a speedometer in which 0 is very slow while 9 is very fast.

It should also be noted that an operator may vary each or all of the rates from program to program without changing any other adjustment in the instrument or influencing other programs.

The DISP phase is lit in display 16 when the program is showing the amount of fluid to be dispensed.

The MEM phase is lit in display 16 when the instrument requests a memory location or is displaying a memory location.

Referring again to FIG. 2, there is illustrated therein four operating mode arrays, which are P/D, DISP, ASP/WSH and PRIME. These four instrument modes are displayed in conjunction with the SELECT mode key 24. The particular operating modes are described as follows:

The PRIME mode is the mode in which the instrument primes the wetted surfaces and is also the mode in which the instrument receives basic operating information of syringe sizes and speeds from an operator.

The P/D mode or pipette/dilute mode is the basic mode of drawing in a sample from a hand probe, drawing in a specified amount of reagent, and then dispensing all of both the reagent and sample.

The DISP mode, or dispense mode, is the mode in which the instrument draws in a specified amount of reagent, then dispenses it through the hand probe. The ASP/WSH mode, or aspirate/wash mode, is used in sample transferring. A sample is drawn in from the probe tip and then dispensed. Then, on a signal from a hand probe switch, the reagent syringe dispenses a wash to cleanse the tip.

The SELECT MODE key 24 of FIG. 2 is pressed to select any one of the operational modes defined above. By pressing key 24 the PRIME light goes out and the P/D light goes in in display 14. By pressing SELECT MODE key 24 again, the system will sequence the display to DISP, then to ASP/WSH, and then to PRIME.

Still referring to FIG. 2, the RECALL key 22 is used to recall a program stored in a specific memory location. For example, if the program stored in memory location is 5, an operator need only press RECALL, then "5", then ENTER. The instrument will immediately display memory location 5, the correct mode and the READY lamp will be lit, and the system is ready to proceed.

The REPEAT key 20 is an important command key, since it allows an operator to modify the basic pattern of one of the operating modes described above. The REPEAT key is used to repeat specific phases in each operating mode, and can be easily programmed by an operator.

Referring now to FIG. 3, a block diagram of the control system is depicted which controls the overall operation of the digital dilution system depicted in FIG. 1.

In a preferred embodiment, the control system for the digital dilution apparatus is based upon an 8-bit Z80 microprocessor 80, as depicted in FIG. 3.

The operating program (which is typically factory installed) is stored in a non-volatile EPROM 82. The program can then be stored indefinitely in EPROM 82 and will not be lost whether the power is on or off.

Programs or instructions entered by an operator through the keyboard 88 (which corresponds to the front panel 14 of FIG. 2) are stored in a CMOS Static RAM 84 in FIG. 3 through interface 86 and bus 100. The stored instructions are retained in RAM 84 until altered by the operator. Instructions coming to a remote station from a master station 104 or from an optional I/O port 108 are also stored in RAM 84.

As can be seen in FIG. 3, peripheral interface 86 communicates with keyboard display 88 and in addition provides appropriate power supply control signals through power driver circuit 90 to the stepping motors and valve motors 90.

Power is then supplied to the control system of FIG. 3 through power supply circuit 92, which could receive its power supply in the form of 100–240 VAC through AC line filter 94.

The control functions in FIG. 3 are interconnected through common bus circuit 100 which will be explained in more detail in conjunction with the schematic diagram of the control system depicted in FIG. 4.

In FIG. 3, bus 100 interconnects with optional remote equipment, such as circuit 104, through a USART (Universal Synchronous-Asynchronous Receiver-Transmitter) circuit 102. Similarly, additional optional remote control devices can be interconnected with the control system via bus 100, I/O circuit 106 and additional circuits 108.

Figure 4:
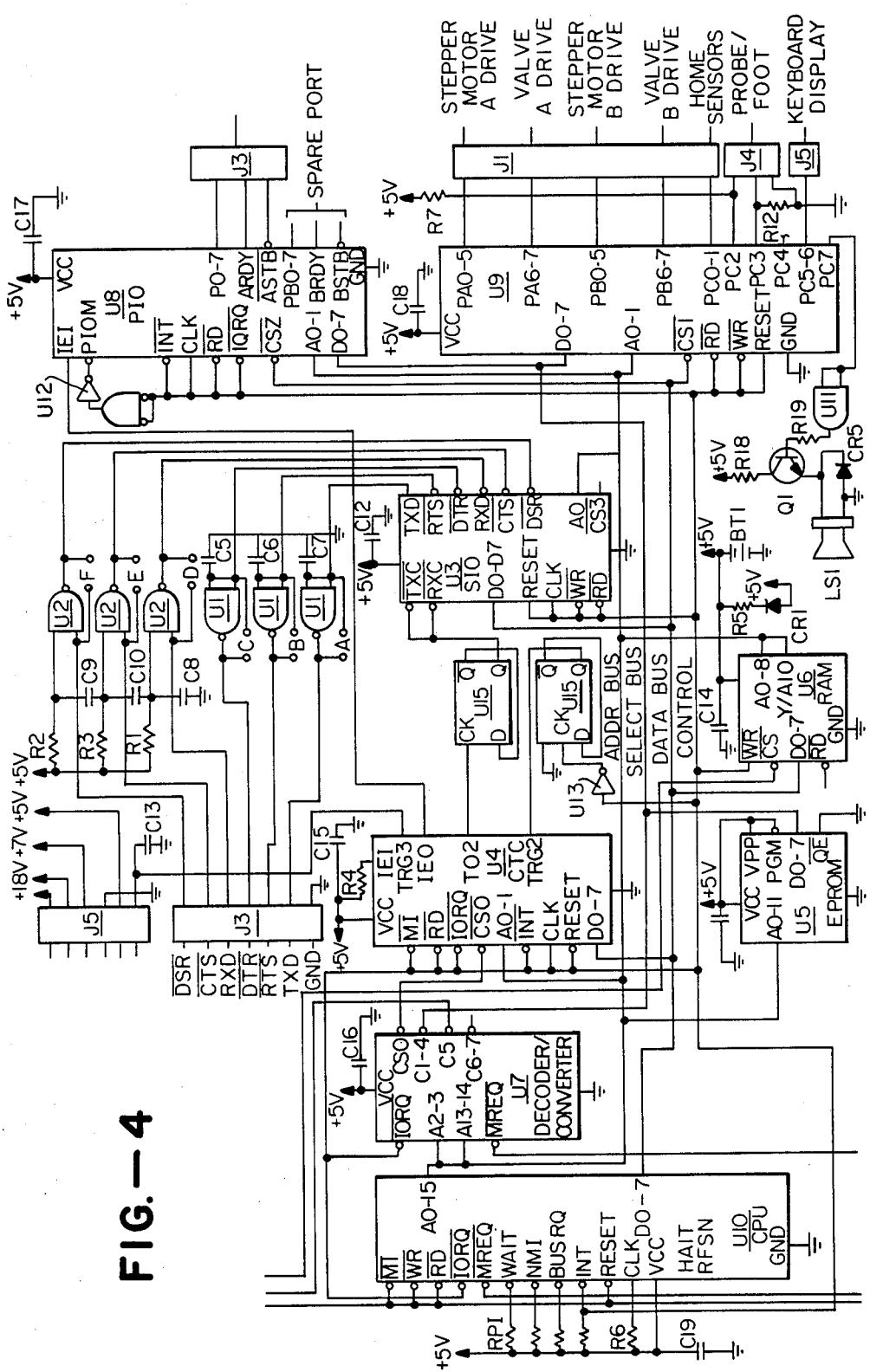
FIG. 4 depicts a schematic diagram of the control system of FIG. 3.

Referring now to FIG. 4, a more detailed schematic diagram of the control system of FIG. 3 is depicted.

In FIG. 4, address bus (A0–A15) is 16 bits. CPU U10 is the source of the control information signals, and EPROM U5 and RAM U6 receive the address control signals, which select the locations in the respective memory to read or write data. Address signals A0 and A1 select channels or control other functions and connect to every chip depicted in FIG. 4.

Address signals A2, A3, A13 and A14 connected to chip U7 (a two to four line decoder circuit). The outputs of decoder U7 are the chip select signals CS0–CS5, which select or activate one chip at a time as the CPU U10 services them.

All the circuits in FIG. 4 are connected to a data bus D0–D7, an 8-bit tri-state, bi-directional bus. Numbers or data such as syringe sizes, dispense rates, amount to aspirate, and number of times to repeat, pass over data bus D0–D7 to or from the CPU U10.

The particular functions of the logic circuits illustrated in FIG. 4, together with their specific unit numbers, are illustrated in Chart I below.

CHART I

| U# | Types | Name and Function |
|---|---|---|
| U10 | Z80, Mostek MK3880 | CPU (Central Processing Unit). U10 cycles addresses, receiving data or sending data at each address, based upon the computation just made. The input data is the "program" entered by the operator, the instructions previously stored in EPROM U5, real time facts such as hand probe operations, and home sensor readings. Outputs on the data bus D0–D7 are display readings, valve and stepping switch operations, and the like. |
| U4 | Z80,CTC, Mostek MK3882 | Counter Timer circuit. Counter U4 decodes the keyboard output-a different frequency for each key pushed. |
| U9 | Z80 PPI, 8255A | Programmable Peripheral Interface. Interface U9 interfaces the real time devices. Signals from the hand probe and the home sensors are converted to data on data bus D0–D7. In the other direction, data bus signals are output to the valve motors, stepping switches, display and audio speaker. |
| U8 | Z80 PIO MK3881 | Parallel Input/Output. The 8-bit bus D0–D7 is bi-directional with handshaking signals, used to add custom peripheral devices or a computer interface. |
| U3 | Z80 SIO, 8251A | USART (Universal Synchronous/Asynchronous Receiver Transmitter). USART U3 converts the system information from data bus D0–D7 into RS 232 protocol, but at 5-volt levels. USART U3 can interface with an external device. |
| U1 | 1488 | Line Drivers. Line drivers U1 convert the 5-volt levels from USART U3 to ±12 volts for an RS 232 line. |
| U2 | 1489 | Line Receivers. Line receiver U2 converts the received RS 232 signals to standard 5-volt levels for USART U3. |
| U5 | 2764 | 8K EPROM (Electrically Programmable Read Only Memory. Programmed instructions are stored in EPROM U5, and are erasable only under ultraviolet light. When selected, EPROM U5 outputs an 8-bit word onto the data bus D0–D7 from the addressed memory cells. |
| U6 | 6516 | CMOS Static RAM (Random Access Memory). CMOS is the process used to make this low power device. When selected, RAM U6 reads the contents of the addressed location onto the data bus D0–D7, if WR is HI, or writes data into the location if WR is LO. A 3.6 volt battery BT1 soldered to the card powers the RAM even when the AC is off, and retains the stored data. The battery BT1 is charged when the AC is on. |
| U7 | 74LS139 | Two input to four output converter. Each section of converter U7 converts two addresses to four chip select signals (CS0–CS7). |

Referring now to FIG. 5, a schematic diagram for a stepper motor drive circuit is illustrated. The present invention utilizes, in one embodiment, two stepper motors. However, for simplicity, only one schematic diagram for each of the stepper motors is illustrated in FIG. 5, although it should be understood that a separate stepper motor logic circuit is required for each stepper motor. In order to provide highly accurate fluid dispenses, a hydraulic control system will be described in conjunction with the stepper motor schematic illustrated in FIG. 5.

Each stepper motor has four windings, driven in a sequence of 1-2-3-4 for one direction or rotation, and 4-3-2-1 for the reverse direction. Both ends of the windings are switched by power transistors. Each stepper motor is controlled by processor 80 of FIG. 4.

In FIG. 5, transistors Q2 and Q3 supply a high voltage (forty volts) pulse to winding W1 on stepper motor A and are then cut off. Transistor Q10 continues to supply a low voltage (seven volts) pulse for the time required for the speed of operation. Similarly, transistor Q11 drives winding W2. The timing waveforms for the motor pulse timing are illustrated in FIG. 6.

In order to supply enough power to drive the power transistors directly, amplifiers Q2, Q4 are used. When the current is turned off, the windings W1, W2 generate high voltage inductive kicks. Consequently, Zener diodes CR8 and CR9 clamp the voltages to ground to protect transistors Q10, Q11 respectively from those surges.

The combination of a two voltage drive to the stepper motor, along with the proper software to get enough current flowing in the motor, provided the following:

1. The ratio of high voltage pulse width (Q3) to low voltage pulse width (Q10) is adjusted so that average power applied during each step is just enough energy to provide for the acceleration (deceleration) load, friction load, and hydraulic load.
2. By so tailoring the power input so that excesses of power are not present, the problems of resonance are reduced.
3. The last pulse applied to the motor contains more energy (high voltage applied for large % of pulse width) than is required to move the fluid. The result is that the stepper motor "overshoots" and then is snapped back into place. The effect on the hydraulic stream is to push fluid out the end of the tip and then pull back creating an automatic air space (known as an air pig) at the end of the tip. This creation of the air pig is aided by items 4 and 5 below.
4. The programmed deceleration ramp created by successive pulses with different pulse widths and different high voltage/low voltage ratio causes the stepper motor to slow down faster than the hydraulic stream slows down. The result is that the water cavitates, that is, air comes out of solution because of vacuum created by fluid continuing to move faster than the syringe. When the forward fluid motion stops, the vacuum pulls the fluid back into the tube, helping to create an air pig.
5. The orifice on the dispensing tube is adjusted so that it is small enough to get a velocity with enough energy ($\frac{1}{2} MV^2$) to cause cavitation—but not too small to raise the fluid friction enough to prevent cavitation.

As indicated above, the stepper motors are driven with a dual voltage supply, as illustrated in FIG. 6.

When it is desired to run a stepper motor at high speed, transistors Q3 or Q5 in FIG. 5 are turned on to overcome the inductance of the motor.

As indicated in FIG. 6, proper hydraulic operation can be achieved because of the fact that the relative amount of time that the high voltage (40 volts) is on relative to the low voltage (7 volts) can be controlled. The proper hydraulic operation thus increases the power. The stepper motor is more efficient because only a single winding is driven at one time, which results in more stability, yet still provides enough power.

Figures 7, 8B:
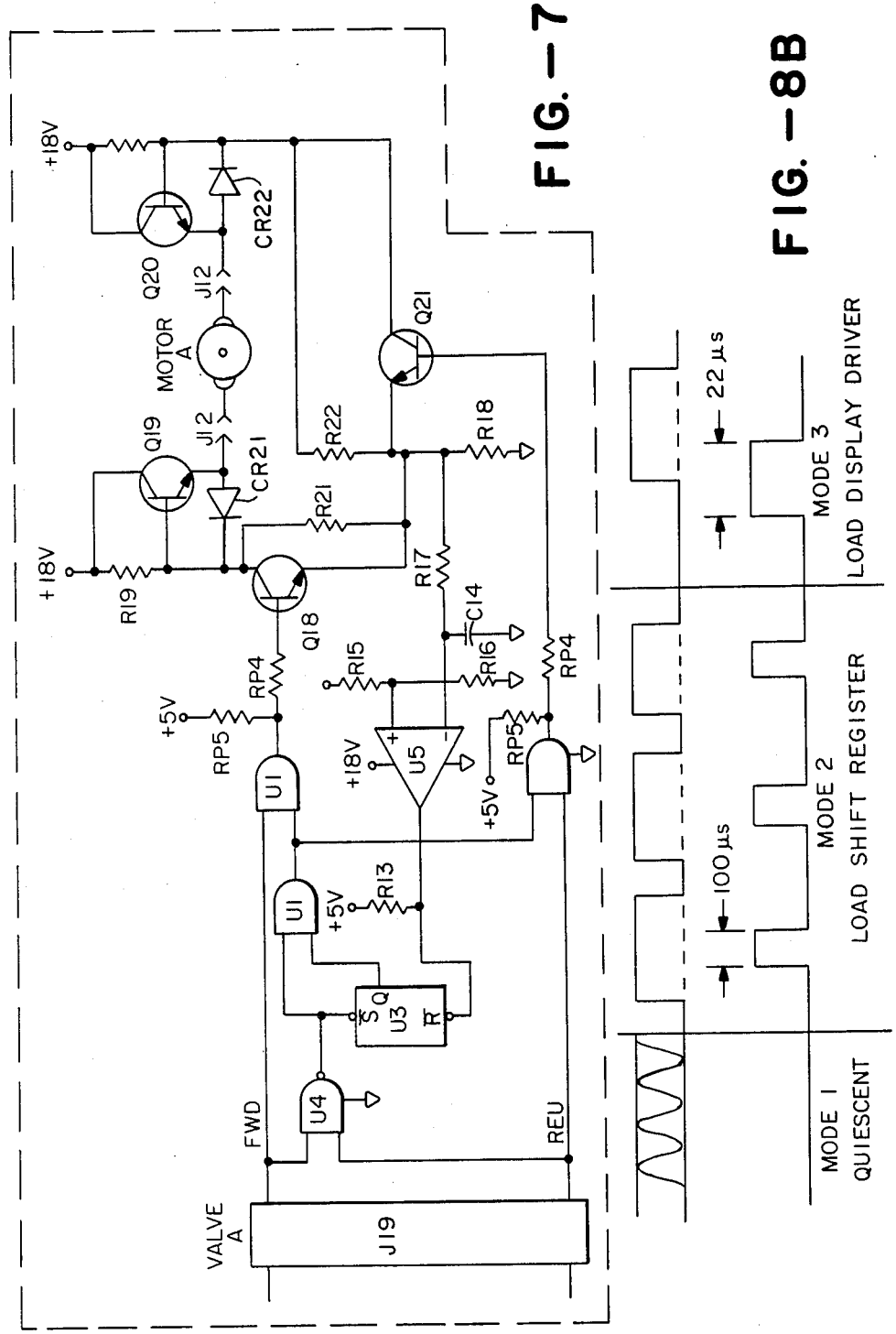
FIG. 7 depicts a schematic diagram for a valve motor drive circuit.
FIG. 8B depicts a timing diagram illustrating the operation of the valve motor drive circuit of FIG. 7.

Referring now to FIG. 7, a schematic diagram for a valve motor drive circuit is illustrated. As with the stepper motor logic circuit of the present invention, the system includes a separate valve motor drive circuit, such as illustrated in FIG. 7, for each valve. It should be therefore understood that a separate circuit is used for the additional valve motor drive.

The drive circuit depicted in FIG. 7 amplifies the signal from the PPI interface circuit U9 of FIG. 4, connecting the valve motor from the 18 volts regulated to ground, and reversing the current direction through the motor to change the valve rotation.

In FIG. 7, four NPN power transistors, Q18–Q21, switch the 18 volts through valve motor A. With the valve at rest, both inputs from the PPI U9 are in a low state. They go high momentarily to set flip-flop U3 and hence turn the valve. If the FWD signal stays in a high state, transistor Q18 is turned on, and transistor Q21 is turned off. Current flows from 18 volts, through transistor Q20, the valve motor (from right to left as indicated in FIG. 7), transistor Q18 and resistor R18 to the common connection.

When the motor reaches the limit of travel and stalls, the current through the winding rises, increasing the voltage across resistor R18. This voltage increase is detected by comparator U5, and resets flip-flop U3, shutting off transistor Q18 and stopping the current flow.

The reverse operation (REV) is similar: current flows from 18 volts through transistor Q19, the valve motor (this time in the opposite direction, from left to right), through transistor Q21, resistor R18 again to the common connection. After the motor stops, comparator U5 again switches from a high to low state to stop the current.

The advantage of this bi-polar motor drive circuit is (1) it automatically shuts off motor drive current when the motor stalls without requiring external sensors, and (2) it is not possible to turn pairs of transistors on which cause a short on the power supply and usually self-destruct the circuit. Hence, the circuit is more reliable and less trouble prone than standard bridge circuits. In FIG. 7, diode CR22 connected between the emitter and base of transistor Q19 turns off transistor Q19 automatically if transistor Q18 is conducting. This feature eliminates the additional transistor and associated resistors usually used to drive the top transistor in a bridge, and it also prevents both transistors from being turned on at the same time—a potential problem in most other bridge circuits.

Figure 8A:
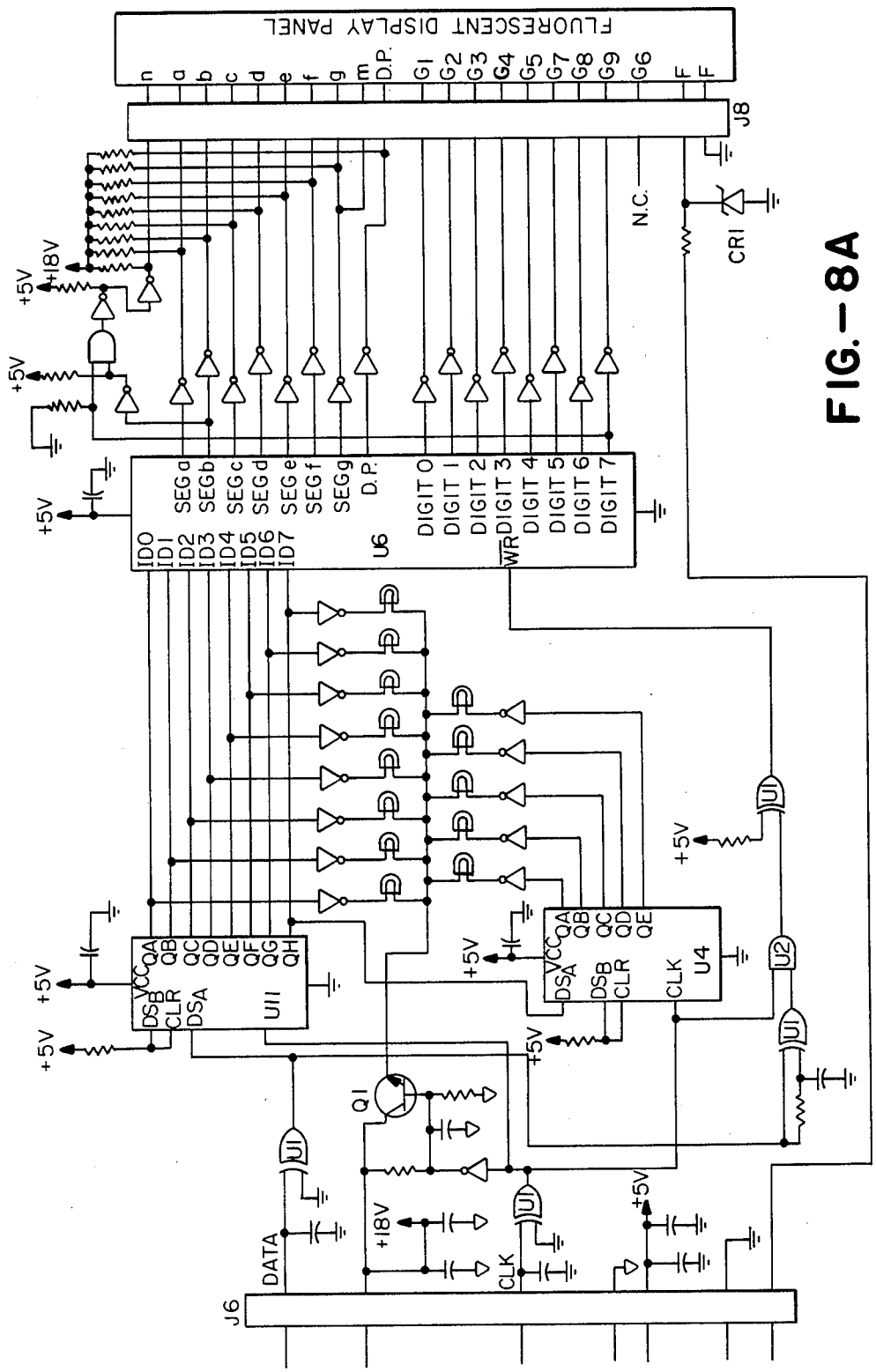
FIG. 8A depicts a schematic diagram of the keyboard lamp display of FIG. 2.

Referring now to FIG. 8B, a timing diagram illustrating the indicator lamp timing is depicted in conjunction with FIG. 8A.

In FIG. 8B, an incoming DATA signal drives the control panel in three modes as depicted.

In the first mode, the display is in a quiescent state, there is no clock signal and the data is in a "don't care" state.

During the second mode, the clock is short (approximately 100 microseconds) and data is loaded into shift register U4 of FIG. 8A.

Figure 9:
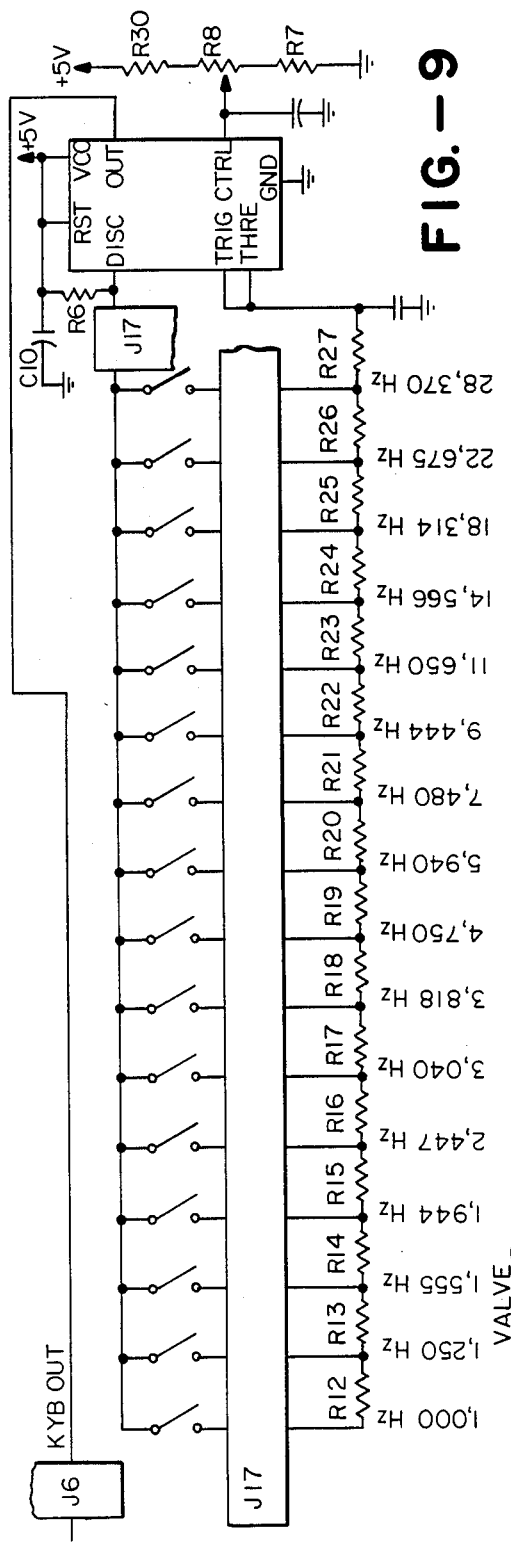
FIG. 9 depicts a resistor array for inputting data into the apparatus of FIG. 2.

In the third mode, the clock is about 200 microseconds, and the display driver U6 of FIG. 9 is loaded, turning on the displays.

Referring now to FIG. 9, a resistor array is depicted to illustrate the input of data from the keyboard 16 of FIG. 2.

In FIG. 9, the resistor array creates a different voltage for each key pressed. A voltage divider network is formed, and the voltage is applied to the monostable counter/timer circuit U10, which generates a square wave with frequency proportional to the particular voltage. Circuit U10 forms a KYB OUT signal which goes to CTC circuit U4 of FIG. 4, which counts the pulses to determine which key was pressed.

Figure 10:
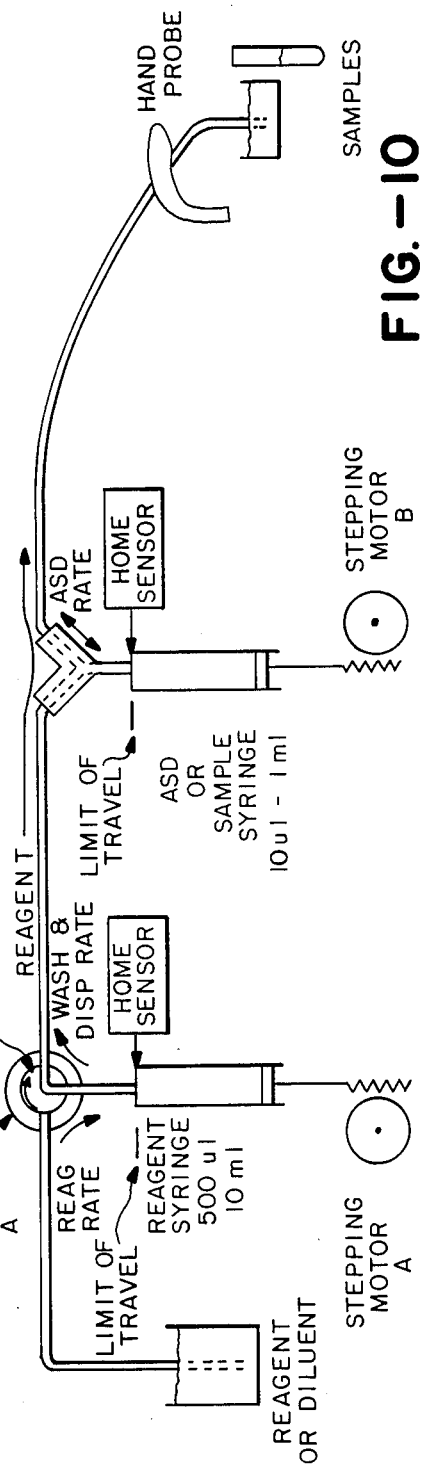
FIG. 10 depicts a diagram illustrating fluid transfer according to the present invention.

Referring now to FIG. 10, a diagram illustrating fluid transfers according to the present invention is depicted.

A dual syringe version is depicted in FIG. 10. A single syringe version typically would only have a reagent syringe installed.

In FIG. 10, a selection of reagent or sample, and the direction of flow is determined by the position of valve A, and the direction of travel of the syringes. Valve A has two positions, one to connect the reagent supply to the reagent syringe, and the other to connect the reagent syringe to the hand probe via the crossflow manifold.

The reagent syringe has the larger volume of the two syringes, since the sample is often diluted by ratios of up to 500:1. The sample syringe depicted in FIG. 10 is smaller for the smaller volumes, and also for greater accuracy.

All tubing is connected to the fluid system components by a screw fitting (not shown) and tubing ends are flared to insure that the seal is secure. The tip of the tube at the hand probe is tapered to a specific profile to provide least sample-to-sample carryover and a good air pig.

Still referring to FIG. 10, illustrative sequences of operation will be described briefly to illustrate various features of the present invention.

At power on, the system should be primed. If the system is properly maintained, one prime sequence is typically sufficient. During this operation, reagent is drawn into the system and flushed out through the hand probe.

For a pipette/dilute operation, a volume of sample fluid is drawn in by the sample syringe, and the correct amount of reagent for the dilution is drawn in through the reagent tube. When both syringes go to the top position, with valve A set to block the reagent port, the correct amount of sample and diluent are dispensed through the probe tip.

For a dispense operation, a selected volume of reagent is drawn in by the reagent syringe. Valve A then changes position and the syringe goes back to the top position, dispensing the reagent through the hand probe tip.

For an aspirate/wash function, a selected volume of sample fluid is drawn into the probe tip by the sample syringe. This fluid is dispensed through the hand probe tip. The system is then cleaned by passing reagent through the hand probe tip.

Referring again to FIG. 10, the digitally controlled pipetter diluter employs a "home" search that allows the seal of the syringe plunger to make close contact with top of the syringe. This method is accomplished through software that steps the syringe up, counts the distance or steps down to the home sensor. This position is then reconfirmed by repeating the test sequence with the newly known distance or offset. This offset is then used to find a very close position without actually contacting the syringe top which would possibly cause some variance in the sample volume. This position or offset is re-established each time the diluter is reinitialized which occurs at any time a syringe is changed because of variances in different syringe volumes as well as changes from syringe to syringe of the same volume. The slight differences are compensated for by software control thereby creating a greater amount of precision without requiring a mechanical adjustment upon changing syringes.

In FIG. 10, if the syringe is at or near the top of movement, the syringe will drive down to the transition point of the "home" sensor. If, in the starting position, the syringe drive is below the sensor, the syringe will start going up. The up motion is accomplished at a high speed until the sensor is encountered. At the point of encountering the transition point of the sensor, the drive will go up in a low power mode. It will continue to go up for 120 steps of the drive which in all cases will top out the seal to the very top of the syringe movement. The syringe then turns around and moves down, the drive moves down counting steps until the sensor transition point is located.

This initial number is reduced by subtracting several steps and reverified. If the reverification says its O.K., then that is used as the offset from the top of the sensor. This allows a floating "home" or zero reference position. The syringe moves essentially past the sensor and then actually into mechanical stops, which are illustrated in FIG. 10 as "Syringe Limit of Travel". Then, the diluter counts down until it sees the sensor and subtracts a few steps to make sure that the seal does not hit the mechanical stop. The actual subtraction is on the order of several steps, which allows for topping out of phase to catch up its correct phase position.

In order to more clearly describe the capabilities of the present invention, a series of processing functions will be described in conjunction with the previous description and the drawings. It should be kept in mind that the present invention does not require the capabilities of a highly skilled operator in order to perform various dilution functions such as described above.

Suppose an operator wishes to dispense 75 microliters (75 ul) of reagent into 19 cuvettes. The operator will use the DISP (Dispense) mode as follows:

| PHASE | PRESS |
|---|---|
| (1) Reag Rate | 9 ENTER |
| (2) Reag | 1000 ENTER |
| (3) Delay | 0 ENTER |
| (4) Disp Rate | 5 ENTER |
| (5) Disp | 75 ENTER |
| (6) Mem | REPEAT/REPEAT |
| (7) Disp | 19 ENTER |

R code flashes on display and memory waits for the operator to enter the number of dispenses desired.

| | |
|---|---|
| Disp (R flashing) | 19 ENTER |
| Mem | 8 ENTER |

Assuming the operator does not want any time delay, he will ENTER "0" into the system.

Assuming a dispense rate of "5" (which is a medium rate), the operator ENTERs "5" into the system.

To instruct the system that the operator wishes to dispense the 75 ul of reagent, the operator ENTERs "75" into the system.

In the preferred embodiment of the invention, because multiple dispenses are desired, the operator presses the "REPEAT" key 20 of FIG. 2 twice as indicated above.

The operator then will indicate a dispense (DISP) number of "19" to indicate the 19 cuvettes which he desires dispensing of the reagent.

The system flashes the "R" code and the memory waits for the operator to enter the number of dispenses desired, which is then located, in this particular instance, in memory location "8".

If the operator desires to edit the "program," he merely presses the ENTER key 18 to verify the program contents. When the display comes to DISP, the display will show

R16 8 0075

This thus indicates the system will repeat 16 times the program in memory location 8 with 75 ul per dispense. The operator will then find that the actual dispensing can be done as fast as he moves his hand from receptacle to receptacle and pressing the hand probe switch.

As another example, suppose an operator wishes to process an indefinite number of dispenses. By pressing the REPEAT key 20 three times in succession, an operator can set the repeating function for an indefinite number of dispenses. This mode is particularly useful when a very large number (uncounted) test tubes are to receive a reagent solution. Also, because the display adds the total amount dispensed as the process ensues, that particular operation is useful for titrating.

As an example, with a 5 ml (milliliter) syringe on the reagent side, a titration can be performed as follows:

| | | DISP MODE - READY ENTER |
|---|---|---|
| (1) | Reag Rate | 9 ENTER |
| (2) | Reag | 5000 ENTER |
| (3) | Delay | 0 ENTER |
| (4) | Disp Rate | 9 ENTER |
| (5) | Disp | 100 ENTER |
| (6) | Mem | REPEAT REPEAT REPEAT Display Flashes R 99 |
| | Mem | 10 ENTER |
| | READY | |

Because the code section of the display is one embodiment allows two digits, 99 is shown above. However, the counter will turn over after counting through 99.

The actual dispensing will proceed nearly as fast as an operator can press the hand probe switch or, if desired, the operator can hold the hand probe switch down and the instrument will dispense at a rate of approximately one dispense per second (depending upon volume).

The display will add the total volume dispensed as the dispensing proceeds. If an operator is performing a titration as in the example above, then this number may be used in his calculations after N point has been reached.

When multiple reagents are used, the reagent syringe may end in mid-stroke. In the indefinite repeat type of program, the instrument does not signal to "know" it has finished. However, the operator merely touches the CLEAR key 26 and the instrument will reset the syringe to top and stand ready for the next selection.

What is claimed is:

1. Digital dilution apparatus comprising:
   processor means including memory means for storing a series of programmed instructions which correspond to operator-controlled general dilution processing requests,
   keyboard input means having a plurality of function display indicators where each of said indicators corresponds to a specified liquid sample processing function for communicating said operator-controlled general dilution processing requests to said processor means,
   output means,
   said processor means responsive to said dilution processing requests for generating a series of communications to said output means inquiring of the specific nature of said processing requests,
   said input means responsive to said series of communications for entering operator-controlled repeatable specified processing mode of operation requests to said processor means such that actuation of one of said function indicators serves to generate repeatable specific processing requests,
   said processor means responsive to said entered requests for processing said specified repeatable dilution processing requests.

2. The apparatus of claim 1 including
   a reagent solution container,
   a reagent syringe,
   a first stepper motor, and first control means for controlling the transfer of reagent solution to and from said reagent syringe.

3. The apparatus of claim 1 including a hand probe and wherein said first control means includes a first valve and means for changing the position of said first valve to connect said reagent syringe to said hand probe or to said reagent solution container.

4. The apparatus of claim 3 including a sample solution container, a sample syringe, a second stepper motor, and second control means for controlling the transfer of sample solution from and to said sample syringe.

5. The apparatus of claim 4 wherein said second control means includes a cross flow manifold and means for changing the position of said manifold to connect said sample syringe to said sample solution container.

6. The apparatus of claim 1 wherein said reagent-syringe and said sample syringe are cassette mounted to facilitate replacement thereof.

7. The apparatus of claim 1 including means for editing said operator-controlled processing requests.

8. The apparatus of claim 1 wherein said repeatable mode of operation is a prime mode.

9. The apparatus of claim 1 wherein said repeatable mode of operation is a pipette/dilute mode.

10. The apparatus of claim 1 wherein said repeatable mode of operation is a dispense mode.

11. The apparatus of claim 1 wherein said repeatable mode of operation is an aspirate/wash mode.

12. Digital dilution apparatus comprising:
    processor means including memory means for storing a series of programmed instructions which correspond to operator general dilution processing requests,
    input means for communicating said operator-controlled general dilution processing requests to said processor means,
    output means,
    said processing means responsive to said dilution processing requests for generating a series of communications to said output means inquiring of the specific nature of said processing requests,
    said input means responsive to said series of communications for entering operator-controlled specific processing requests to said processor means,
    said processor means responsive to said entered requests for processing said specified dilution processing requests,
    a reagent syringe having reagent solution, and
    means for sensing a position of reagent solution in said reagent syringe.

13. Digital dilution apparatus comprising:
    processor means including memory means for storing a series of programmed instructions which correspond to operator-controlled general dilution processing requests,
    input means for communicating said operator-controlled general dilution processing requests to said processor means,
    output means,
    said processor means responsive to said dilution processing requests for generating a series of communications to said output means inquiring of the specific nature of said processing requests,
    said input means responsive to said series of communications for entering operator-controlled specific processing requests to said processor means,
    said processor means responsive to said entered requests for processing said specified dilution processing requests,
    a reagent solution container,
    a reagent syringe,
    a first stepper motor, and first control means for controlling the transfer of reagent solution to and from said reagent syringe, and
    means for applying a first high-voltage pulse and a second low-voltage pulse to said stepper motor to provide sufficient power and stability for controlling the operation of said stepper motor.

14. The apparatus of claim 13 wherein said stepper motor includes bipolar motor drive circuit means.

15. Digital dilution apparatus comprising:
    processor means including memory means for storing a series of programmed instructions which correspond to operator-controlled general dilution processing requests,
    numeric keyboard display input means for communicating said operator-controlled general dilution processing requests to said processor means,
    output means,
    said processor means responsive to said dilution processing requests for generating a series of communications to said output means inquiring of the specific nature of said processing requests,
    said input means responsive to said series of communications for entering operator-controlled specific processing requests to said processor means,
    said processor means responsive to said entered requests for processing said specified dilution processing requests, and
    two-wire encoding means for driving said numeric keyboard display means.

16. Digital dilution apparatus comprising:
processor means including memory means for storing a series of programmed instructions which correspond to operator-controlled general dilution processing requests,
input means for communicating said operator-controlled general dilution processing requests to said processor means,
output means,
said processor means responsive to said dilution processing requests for generating a series of communications to said output means inquiring of the specific nature of said processing requests,
said input means responsive to said series of communications for entering operator-controlled specified processing requests to said processor means,
said processor means responsive to said entered requests for processing said specified dilution processing requests,
a reagent solution container,
a reagent syringe,
a first stepper motor, and first control means for controlling the transfer of reagent solution to and from said reagent syringe, and
dual cycle, dual voltage motor drive means for driving said stepper motor, said motor drive means including a single winding.

17. In a digital dilutor, the apparatus comprising
a reagent solution container,
a reagent syringe,
stepper motor means,
motor drive control means for controlling the transfer of reagent solution between said container and said reagent syringe,
means for sensing a first reference position of reagent solution in said reagent syringe where said first reference position is close to a home position of said syringe,
means for stepping said syringe past said first reference position,
means for counting a first sufficient number of steps to cause an overshoot past said home position,
means for stepping said syringe back a second number of steps to said first reference position,
means for determining the difference between said first number and said second number of steps, and
means for repetitively processing the stepping of said syringe until the number of first and second steps are nearly the same.

18. The apparatus of claim 17 including means for reducing said first number of steps.

19. In a digital dilutor, the apparatus comprising
a reagent solution container,
a reagent syringe,
stepper motor means,
motor drive control means for controlling the transfer of reagent solution between said container and said reagent syringe, said control means including means for applying first high-voltage pulses of a first duration and second low-voltage pulses of a second longer duration to said stepper motor means to provide sufficient power and stability for hydraulically controlling the operation of said stepper motor means.

20. The apparatus of claim 19 wherein said control means includes means for controlling the ratio of said high-voltage pulse widths to said low-voltage pulse widths such that the ratio of said high-voltage pulse widths to said low-voltage pulse widths is adjusted so that average power applied during each step is just enough energy to provide for the acceleration or deceleration load, friction load, and hydraulic load.

21. The apparatus as in claim 20 including means for applying pulses to said stepper motor means such that the last pulse applied to said stepper motor means contains more energy than is required to move the fluid.

22. The apparatus as in claim 21 including means for applying a programmed deceleration ramp created by successive pulses with different pulse widths and different high-voltage/low-voltage ratio which causes said stepper motor means to slow down faster than the hydraulic stream slows down.

23. The apparatus as in claim 22 including a dispensing tube and wherein the orifice on said dispensing tube is adjusted so that it is small enough to cause cavitation, but not too small prevent cavitation.

24. Digital dilution apparatus comprising
a reagent solution container,
a reagent syringe,
valve motor means connected between said container and said syringe,
valve motor drive control means including a first and a second pair of transistor means for driving said valve motor means in a first and second direction, respectively, and
means for preventing said first and second transistor means from driving said valve motor means at the same time.

25. Digital dilution apparatus comprising
a reagent solution container,
a reagent syringe,
valve motor means connected between said container and said syringe,
valve motor drive control means including a first and a second pair of transistor means for driving said valve motor means in a first and second direction, respectively, and
means for automatically turning off said valve motor drive control means if said motor means stalls.

* * * * *